(12) United States Patent
Gavin et al.

(10) Patent No.: US 8,158,158 B2
(45) Date of Patent: Apr. 17, 2012

(54) COMPOSITE BIOCIDAL PARTICLES

(75) Inventors: David F. Gavin, Cheshire, CT (US);
Craig Waldron, Wolcott, CT (US);
Robert J. Martin, Monroe, CT (US);
George A. Polson, Harwinton, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 10/077,727

(22) Filed: Feb. 15, 2002

(65) Prior Publication Data

US 2002/0110575 A1 Aug. 15, 2002

Related U.S. Application Data

(62) Division of application No. 09/120,664, filed on Jul. 22, 1998.

(51) Int. Cl.
*A61K 33/34* (2006.01)
*A61K 33/24* (2006.01)
*A01N 59/16* (2006.01)

(52) U.S. Cl. ........ 424/630; 424/617; 424/603; 424/600; 424/420; 424/405; 424/400

(58) Field of Classification Search .................. 424/408, 424/630, 617, 603, 600, 420, 405, 400
See application file for complete search history.

(56) References Cited

U.S. PATENT DOCUMENTS

| | | | | |
|---|---|---|---|---|
| 2,786,847 A | 3/1957 | Cislak | ......................... | 260/294.8 |
| 2,809,971 A | 10/1957 | Bernstein et al. | ............. | 260/270 |
| 3,589,999 A | 6/1971 | McRae et al. | ..................... | 210/28 |
| 3,590,035 A | 6/1971 | Damico | ......................... | 260/290 |
| 3,773,770 A | 11/1973 | Damico | ......................... | 260/290 |
| 4,323,683 A | 4/1982 | Bolich, Jr. et al. | | |
| 5,057,153 A | 10/1991 | Ruggiero | ..................... | 106/18.33 |
| 5,246,489 A | 9/1993 | Farmer, Jr. et al. | ........ | 106/18.33 |
| 5,298,061 A | 3/1994 | Waldron et al. | ............. | 106/18.33 |
| 5,342,437 A | 8/1994 | Gavin et al. | ................. | 106/18.33 |
| 5,510,109 A | 4/1996 | Tomioka et al. | .............. | 424/421 |
| 5,518,774 A * | 5/1996 | Kappock et al. | .............. | 427/384 |
| 5,540,860 A | 7/1996 | Hosseini et al. | .............. | 252/308 |
| 5,595,750 A | 1/1997 | Jacobson et al. | .............. | 424/421 |
| 5,776,960 A | 7/1998 | Oppong et al. | ............... | 514/345 |
| 5,821,271 A | 10/1998 | Roenigk | .......................... | 521/54 |
| 5,916,947 A * | 6/1999 | Morris et al. | .................. | 524/432 |
| 6,017,936 A * | 1/2000 | Polson et al. | .................. | 514/345 |
| 6,465,015 B1 * | 10/2002 | Mohseni et al. | .............. | 424/489 |

FOREIGN PATENT DOCUMENTS

| | | |
|---|---|---|
| EP | 0034385 A2 | 8/1981 |
| JP | 10025111 A | 1/1998 |
| WO | 94/12034 A1 | 6/1994 |
| WO | WO 98/41505 | 9/1998 |
| WO | WO 98/47372 | 10/1998 |

* cited by examiner

*Primary Examiner* — T. D. Wessendorf
(74) *Attorney, Agent, or Firm* — Dale L. Carlson; Wanli Wu; Wiggin and Dana LLP

(57) ABSTRACT

A biocidal composition is disclosed comprising composite particles, each of said composite particles containing a shell and a core, said core comprising a metal or a metal-containing compound wherein the metal is a moiety selected from the group consisting of zinc, copper, bismuth, silver, zirconium, and combinations thereof said shell comprising a pyrithione adduct comprising the reaction product of pyrithione with a portion of said core metal or metal compound. In one aspect, an anti-fouling composition is disclosed comprising (a) an anti-soft-fouling effective amount of copper pyrithione; and (b) an anti-hard-fouling effective amount of a copper-containing salt, or oxide or hydroxide thereof. The present invention also relates to a method of making an anti-fouling composition comprising particles of copper pyrithione and a copper-containing salt that is effective against hard-fouling and soft-fouling organisms.

7 Claims, 1 Drawing Sheet

COMPOSITE BIOCIDAL PARTICLES

CROSS-REFERENCE TO RELATED APPLICATION

This application is a division of U.S. patent application Ser. No. 09/120,664, filed Jul. 22, 1998, the disclosure of which application is incorporated by reference in its entirety herein.

BACKGROUND OF THE INVENTION

1. Field of the Invention

The present invention relates generally to biocidal compositions, and more particularly, compositions comprising composite particles, wherein each of the composite particles contains a shell and a core possessing differing biocidal activity profiles. The core comprises a biocidally active oxidized metal, or metal-containing compound, and the shell comprises a pyrithione salt of the core metal having complimentary biocidal activity to the activity of the core. Select compositions of the present invention, when incorporated into a matrix, such as a paint or other coating composition, provide the matrix with resistance to fouling by organisms of more than one type, thus providing broad spectrum biocidal activity.

2. Description of the Related Art

Certain composite particles containing a biocide are known. By way of illustration, U.S. Pat. No. 5,510,109 discloses an antibacterial/antifungal material carried on a porous particle carrier that is preferably a silica gel particle. As another illustration, U.S. Pat. No. 5,595,750 discloses an antimicrobial composition comprising an inorganic particle having a first coating possessing antimicrobial properties and a second coating providing a protective function for the composition. Heretofore, however, no composite biocide particles have been known, based upon the knowledge of the present inventors, comprising two biocides with differing biocidal activity profiles.

In the marketplace, biocides enjoy wide usage. For example, biocidal compositions are employed in a wide variety of applications, including shampoos, soaps, skin care medicaments, as well as paints, particularly marine paints. Fouling of marine equipment has been a persistent problem for many years. For example, boat hulls, docks, buildings, fishnets and cages, and related marine equipment that are in constant contact with marine water become fouled with algae, barnacles and other marine organisms, and much time and expense is required to remove these organisms.

Generally, marine fouling has been categorized into two broad classes. "Soft-fouling" refers to growth of "soft" organisms, such as algae on marine and coastal equipment and other outdoor structures. "Soft" organisms also include the fungi causing mildew, often co-existing with algae, and typically necessitating the addition of both an algaecide and a fungicide in outdoor coatings such as architectural paints. "Hard-fouling", by contrast, refers to growth of "hard" organisms such as barnacles, and tubeworms. Compounds used to control hard fouling include copper, cuprous oxide, zinc oxide, and copper thiocyanate. As used herein "anti-soft-fouling" refers to an antifouling agent that is effective in reducing or preventing the growth of soft organisms, whereas "anti-hard-fouling" refers to an antifouling agent that is effective in reducing or preventing the growth of hard organisms. Due to the fact that there exist different organisms that cause soft-fouling versus hard-fouling, separate approaches have been taken to address each type of fouling.

Polyvalent metal salts of pyrithione (also known as 1-hydroxy-2-pyridinethione; 2-pyridinethiol-1-oxide; 2-pyridinethione; 2-mercaptopyridine-N-oxide; and pyridinethione-N-oxide) have gained acceptance for use in marine paints and coatings to decrease or minimize soft-fouling. These salts are known to be effective biocidal agents, leading to their wide usage as algaecides, fungicides and bactericides in paints and personal care products such as anti-dandruff shampoos. Generally these salts are only sparingly soluble in water, as typified by magnesium pyrithione, barium pyrithione, bismuth pyrithione, ferric pyrithione, strontium pyrithione, copper pyrithione, zinc pyrithione, cadmium pyrithione, and zirconium pyrithione. The most widely used divalent pyrithione salts are zinc pyrithione and copper pyrithione. Synthesis of polyvalent pyrithione salts is described in U.S. Pat. No. 2,809,971 incorporated herein by reference in its entirety. Other patents disclosing similar compounds and processes for making them include U.S. Pat. Nos. 2,786,847; 3,589,999; 3,590,035; and 3,773,770, each of which is incorporated herein by reference in their entireties.

Zinc pyrithione is useful as an antimicrobial agent active against gram-positive, some negative bacteria, fungi, algae and yeasts. Suspensions of zinc pyrithione are also used as antibacterial, antifungal, and antialgael additives to provide soft-fouling protection for paints and other coating compositions. However, zinc pyrithione is not as effective against hard-fouling organisms as might be desired.

Copper pyrithione is sold commercially as an algaecide and anti-soft-fouling agent for marine paints and coatings as disclosed in U.S. Pat. Nos. 5,246,489 and 5,540,860, both of which are incorporated by reference in their entireties. Copper pyrithione offers several advantages over zinc pyrithione for many applications, notably a lower solubility (about 1 ppm versus 6-10 ppm for zinc pyrithione). The lower solubility of copper pyrithione, as compared to zinc pyrithione, increases its effective availability as a biocidal agent over a longer period of time when exposed to marine environments, and makes it particularly desirable as an anti-soft-fouling agent. However, copper pyrithione is not as effective in preventing hard-fouling as might be desired. To address this shortcoming, combinations of soft-fouling and hard-fouling agents have been manufactured. However, to date, these combinations have not been entirely successful.

Combinations of zinc pyrithione or copper pyrithione and copper compounds such as cuprous oxide, copper hydroxide, or copper thiocyanate are known to be useful antifouling agents when formulated into marine paint compositions to control both hard- and soft-fouling. Such a paint composition is disclosed in U.S. Pat. No. 5,057,153, herein incorporated by reference in its entirety. However, paint compositions which include zinc pyrithione and cuprous oxide antifouling agents tend to form undesirable gels during storage, thereby limiting the useful life of the composition. The gelation problem, and efforts to resolve or mitigate it are described in U.S. Pat. Nos. 5,298,061 and 5,342,437.

Tributyl tin compounds have in the past been demonstrated to be effective in controlling soft-fouling, and to a lesser degree, hard-fouling, organisms. However, tributyl tin compounds are toxic to non-target organisms, and are persistent, thus posing an unwanted environmental hazard.

In addition, these toxic compounds persist in the environment after application and continue to exert their toxic effects for years. Therefore, use of tributyl tin compounds as anti-hard- and antisoft-fouling agents is restricted in many parts of the world. Accordingly, what the paints and coatings community needs is a safer antimicrobial agent that is effective in controlling both soft- and hard-fouling growth simultaneously. In this regard, zinc and copper compounds, such as zinc oxide, cuprous oxide, and pyrithione salts, such as zinc pyrithione or copper pyrithione, have been individually added to antifouling paints. However, such a combination made by separately adding these two components to a paint has been found to provide less performance efficacy (based upon the amounts of individual components added to the paint) than might otherwise be desired. Accordingly, new methodology for providing relatively environmentally safe combinations of anti-hard and anti-soft components within a single biocidal composition package for use in paints and other coatings would be highly desired by the coatings manufacturing community. The present invention provides one answer to that need.

SUMMARY OF THE INVENTION

In one aspect, the present invention relates to a biocidal composition comprising composite particles, each of said composite particles containing a shell and a core, said core comprising a metal or a metal-containing compound wherein the metal is a moiety selected from the group consisting of zinc, copper, bismuth, silver, zirconium, and combinations thereof, and said shell comprising a pyrithione adduct comprising the reaction product of pyrithione with a portion of said metal or metal-containing compound from said core. The shell component provides complimentary biocidal activity to the biocidal activity of the core component.

In another aspect, the present invention relates to a biocidal composition that is effective against both soft fouling and hard fouling comprising composite particles, each said composite particle containing a shell and a core, said core comprising a metal or a metal-containing compound comprising a moiety selected from the group consisting of zinc, copper, bismuth, silver, iron, titanium, aluminum, zirconium and combinations thereof, and said shell comprising a pyrithione salt comprising pyrithione and said moiety.

In yet another aspect, the present invention relates to a method of making a biocidal composition comprising reacting pyrithione or a water-soluble salt of pyrithione and an essentially water insoluble metal or metal-containing compound (such as a copper salt, oxide or hydroxide), optionally in the presence of a surfactant, to produce a composition comprising the above described composite particles. In one application, the resulting composition is advantageously effective against hard-fouling and soft-fouling organisms.

In still another aspect, the present invention relates to a method of reducing or inhibiting the growth of hard and soft organisms on a surface which comprises contacting the surface with an antifouling composition comprising the above-described composite particles.

In another aspect, the present invention relates to a shampoo, soap, skin care medicament, or combination thereof, comprising a surfactant and composite particles, each said composite particle containing a shell and a core, said core comprising a metal or a metal-containing compound comprising a moiety selected from the group consisting of zinc, copper, bismuth, silver, iron, titanium, aluminum, zirconium and combinations thereof, and said shell comprising a pyrithione salt comprising pyrithione and said moiety. When employed for this purpose, the composite particles offer the potential for reduced skin absorption and equivalent skin or hair surface coverage vis-à-vis a simple mixture of the biocidal additives.

In still another aspect, the present invention relates to a coating composition comprising an aqueous base medium (such as a latex) or an organic solvent based resin-containing base medium and an antifouling composition comprising the above-described composite particles.

In yet another aspect, the present invention relates to a coated substrate comprising a substrate and a coating thereon, said coating comprising the above-described composite particles.

These and other aspects will become apparent upon reading the following detailed description of the invention.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
FIG. 1 is a comparison photomicrograph of cuprous oxide particles viewed at 5,000× magnifications.

It now has been surprisingly found, in accordance with the present invention, that a solution is provided to the problem of controlling both soft-fouling and hard-fouling marine organisms in a single biocidal composition comprising composite particles. Select composite particles provide antifouling efficacy against both hard-fouling and soft-fouling organisms that are typically encountered in a marine environment. The composite particle structure has been found to be particularly effective in providing controlled release of the core biocide into the aqueous environment that is present under use conditions for a marine or architectural paint or a personal care composition such as soap or shampoo. As another alternative, composite particles are suitably designed to provide a relatively low-cost biocide by transchelation to provide composite particles having a core of filler or a biocide and a shell of pyrithione, thereby increasing the effective surface area of the pyrithione biocide. When employed in personal care compositions, the composite particles can provide desirable reductions in skin absorptivity relative to a mixture of the individual biocidal components. The composite particles prepared in accordance with the present invention are also advantageously employed in marine paints, architectural coatings and adhesives and the like, but they also can be tailored for use in other applications such as in personal care items, such as soaps, shampoos and skin care medicaments, and suitable plastic and polymeric substrates. The particle size for the composite particles typically ranges from 1 to 20 microns, advantageously from 1 to 10 microns, in diameter.

The compositions of the present invention avoid the toxicity issues typically associated with tributyl tin compounds currently used to control both hard- and soft-fouling marine organisms. In addition, the compositions of the present invention resist gelation during storage, and therefore can be stored for long periods of time prior to use. The compositions of the present invention provide the additional advantage of a more economical and environmentally preferred rate of delivery of the antifouling components, namely the copper pyrithione component and the copper or oxide or hydroxide component. In one embodiment, cuprous oxide and sodium pyrithione are mixed in an aqueous solvent to produce a composite particle comprising a mixture of copper pyrithione and cuprous oxide wherein the cuprous oxide core is coated with a shell of copper pyrithione.

As used herein, the term "antifouling agent" refers to compounds which substantially reduce or eliminate the growth of marine organisms that attach to structures in contact with marine water. The term "soft-fouling" and "soft-fouling organisms" as used herein refers to those soft marine organisms such as algae, slime, grass and diatoms. The term "hard-fouling" and "hard-fouling organisms" as used herein refers to hard or shelled marine organisms such as barnacles, mussels, bryozoa and tubeworms. The term "anti-soft-fouling effective amount" refers to an amount of a compound which is effective in substantially reducing or eliminating the growth of soft-fouling organisms. Similarly, the term "anti-hard-fouling effective amount" refers to an amount of a compound which is effective in substantially reducing or eliminating the growth of hard-fouling organisms.

As indicated above, the invention relates to an antifouling agent, comprising an antisoft-fouling effective amount of copper pyrithione; and an antihard-fouling effective amount of a copper-containing salt.

Copper pyrithione is among the least water soluble of the pyrithione salts (generally less than 1 ppm in seawater). The zinc salt, by comparison, has a water solubility of about 6-10 ppm, while the sodium salt of pyrithione has a water solubility of about 53% by weight. Copper pyrithione is, therefore, a very desirable component of antifouling marine paints due to its relative insolubility but adequate biocidal efficacy.

The copper-containing core-compound can be a copper or one of its compounds slightly soluble in water up to about 10 ppm. Useful counterions for the copper cation include oxides, sulfides and selenides. Preferable copper-containing compounds that are useful in the invention include cuprous oxide, cuprous sulfide, copper thiocyanate, and copper hydroxide, or copper metal, either coated or uncoated, or surface oxidized. A particularly preferable copper-containing compound is cuprous oxide. Combinations of these copper-containing compounds may also be used in accordance with the invention.

When working with copper compounds, an effective combination of copper pyrithione and another copper-containing salt, oxide, or hydroxide thereof (or copper metal or surface-oxidized copper) is employed in the antifouling composition of the present invention to provide the desired antifouling protection. Preferably, the relative proportions of copper pyrithione and copper containing compound are such that the copper pyrithione partially or completely coats the other copper containing compound to form a shell around that other compound. To achieve this result, the copper-containing metal, oxide, or hydroxide (or combination thereof) component of the antifouling composition of the invention preferably comprises from about 99 to about 60% by weight, more preferably 98 to about 80% by weight, and most preferably 98 to about 90% by weight, all based on the total weight of said antifouling agent, and the copper pyrithione component of the antifouling agent of the invention preferably comprises from about 1 to about 40% by weight, more preferably from about 2 to about 10% by weight, and most preferably from about 2 to about 10% by weight, all based on the total weight of said antifouling agent.

A surfactant or fatty acid may be included in the antifouling agent of the invention to coat the particles to prevent the copper-containing core compound from oxidizing upon exposure to air. Suitable fatty acids and derivatives for use in the present invention include oleic acid, stearic acid, glycerol, lecithin, and the like.

The antifouling composition of the invention may be prepared by a transchelation reaction of pyrithione or a water-soluble salt of pyrithione and a copper-containing minimally soluble salt, or a copper particle. Pyrithione may be used in its acid form, or it may be employed in the form of a water-soluble salt of pyrithione for the desired transchelation reaction. Preferably, the water-soluble salt of pyrithione has a water solubility greater than about 4 ppm. Useful water soluble salts of pyrithione preferably include an ammonium ion or an alkali or alkaline earth metal ion such as sodium or calcium, or magnesium. Accordingly, exemplary water soluble salts of pyrithione include sodium pyrithione, potassium pyrithione, lithium pyrithione, ammonium pyrithione, tert-butyl amine pyrithione, calcium pyrithione, dithiobis (pyridine-N-oxide), a magnesium salt adduct of dithiobis (pyridine-N-oxide), and combinations thereof, to cause transchelation of said pyrithione compound to copper pyrithione. The most preferred water-soluble salt of pyrithione useful in the present invention is the sodium salt (i.e., sodium pyrithione). The amount of pyrithione or water-soluble salt of pyrithione can vary over a wide range and establishing a useful amount is within the capabilities of the ordinary skilled practitioner based on the stoichiometry of the reaction.

As indicated above, suitable copper-containing compounds and hydroxides that are useful in the present invention include cuprous oxide, cuprous sulfide, copper thiocyanate, copper, surface oxidized copper, partially reduced cupric oxide, and copper hydroxide. A particularly preferable copper-surface oxidized copper, containing salt is cuprous oxide. The amount of copper-containing salt present in the reaction may vary depending on the amount of pyrithione or water-soluble salt of pyrithione used in the reaction.

Sufficient pyrithione, or water-soluble salt of pyrithione, must be added to the particle forming reaction to produce enough copper pyrithione to protect against soft-fouling microorganisms and also enough copper-containing salt, hydroxide, or oxide (e.g., cuprous oxide) to be effective against hard fouling organisms, present within a weight range of ratios of from 1:20 to 20:1 (more preferably of from 1:10 to 10:1) of copper pyrithione relative to the copper-containing salt, or oxide or hydroxide thereof. Preferably, the relative proportions of copper pyrithione and copper containing salt are such that the copper pyrithione partially or completely coats the cuprous oxide particle.

Useful media for the reaction include aqueous media such as water, or water in combination with one or more organic solvent(s). Useful organic solvents include alcohols, such as methanol, ethanol, amines such as diethanolamine, ether, esters, and the like, including emulsified combinations of same.

In accordance with the method of the invention, the copper-containing salt and pyrithione or water-soluble salt of pyrithione are mixed in a solvent such as water to produce a mixture of copper pyrithione and copper-containing compound, and preferably, a copper-containing salt particle that is coated with copper pyrithione molecules.

Additional materials, such as dispersants, surfactants, and the like may be added to the reactants during the precipitation or transchelation reaction to prevent agglomeration of the pyrithione salt particles. Alternatively, the dispersant or surfactant may be added at the completion of the reaction to prevent particle agglomeration. Exemplary dispersants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. If desired, the alcohol alkoxylate is suitably end-capped with a lower alkyl group, and such a product is commercially available as POLY-TERGENT SLF-18 surfactant, available from BASF Corporation. Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates.

Other useful anionics are polycarboxylated alcohol alkoxylates, preferably those selected from the group consisting of the acids or organic or inorganic salts of the following: polycarboxylated linear alcohol alkoxylates, polycarboxylated branched alcohol alkoxylates, polycarboxylated cyclic alcohol alkoxylates, and combinations thereof.

Illustrative cationic dispersants include alkyl triammonium halide, non-linear alkyl dimethyl halide and alkyl dimethyl benzyl ammonium halide-containing surfactants. Illustrative amphoteric dispersants include polyglycol ether derivatives, ethoxylate oxazoline derivatives, lauramidopropyl betaine and lecithin.

As will be appreciated by those skilled in the art, suitable blends can be employed in the process of the present invention based on various combinations of the above-described surfactants. The dispersant or surfactant is preferably employed in a total amount of between about 0.05 and 10%, more preferably between about 0.1 and 5%, most preferably between about 0.5 and about 1.5% by weight, based on the total weight of the reaction mixture.

A fatty acid, as described above, may be included in the antifouling agent of the invention to coat the particles to prevent the copper-containing salt from oxidizing upon exposure to air. The fatty acid component may be added to the reaction mixture, or after the particles are isolated, as described in more detail below.

Preferably, the temperature of the reaction should be maintained between about 20° C. and about 80° C., and most preferably between about 25° C. to about 70° C. A particularly useful temperature range is 40° C.-70° C.

The pyrithione composite particles may be isolated from the by-products by filtration of other isolation methods known in the art.

General methods for making a copper-based version of an antifouling agent of the invention include either (a) first producing a water slurry of cuprous oxide, desired aqueous slurry of cuprous oxide, and (b) adding sodium pyrithione, or a solution thereof, to this slurry, to cause transchelation of the sodium and surface generated copper ions and thereby produce adherent copper pyrithione. The sodium pyrithione can be used in crude form such as 15% plant stream in "as produced" or 40% purified form. The cuprous oxide/sodium pyrithione slurry is then mixed for a time sufficient to enable all of the sodium pyrithione to react and transchelate to form adherent copper pyrithione. The solids are next washed to remove any of the water soluble salts. The particles may optionally be coated with a fatty acid or other protectorant such as lecithin to prevent the cuprous oxide from oxidizing to cupric oxide once dried. The product is then filtered, dried. The product is now ready for use in marine paints as an antifouling agent.

A preferred process for carrying out the present invention entails the steps of: (1) charging into a reaction vessel an untreated cuprous oxide slurry, (2) adding crude sodium pyrithione, (3) mixing until all of the sodium pyrithione is reacted, (4) adding a small amount of protective agent to coat the particles, and (5) filtering, washing, drying and milling the product.

Another preferred process for carrying out the present invention entails the steps of: (1) charging into a reaction vessel a fatty acid treated cuprous oxide slurry, (2) adding crude sodium pyrithione, (3) mixing until all of the sodium pyrithione is reacted, (4) filtering, washing, drying and milling the product.

Another process for carrying out the present invention entails the steps of: (1) charging into the reaction vessel some treated cuprous oxide powder then adding water with stirring to make a slurry, (2) adding crude sodium pyrithione, (3) mixing until all of the sodium pyrithione is reacted, (4) filtering, washing, drying and milling the product.

Another process for carrying out the present invention entails the steps of: (1) charging into the reaction vessel a treated cuprous oxide slurry, (2) adding commercial grade sodium pyrithione, (3) mixing until all of the sodium pyrithione is reacted (4) filtering, washing, drying and milling the product.

As another alternative, the composition of the present invention is suitably produced by combining copper pyrithione (in the form of an aqueous dispersion, wet cake or dry solid) with cuprous oxide, or by "co-streaming" the copper pyrithione into the cuprous oxide production. One advantage of using copper pyrithione rather than sodium pyrithione, is that essentially no sodium salts remain in the composition, thus obviating any need for water washing of the product to remove sodium salts.

The copper pyrithione/cuprous oxide composition of the invention is useful as an antifoulant in marine paints and coatings, or as a seed and crop fungicide.

EXAMPLES

The following examples are intended to illustrate, but in no way limit the scope of, the present invention.

Example 1

Preparation of a 1:10 Parts by Weight Copper Pyrithione: Cuprous Oxide Composite Particle Product Made Using Cuprous Oxide Plus Sodium Pyrithione 292.19 grams of a 70% aqueous untreated cuprous oxide slurry was charged into a 1000 ml 3-neck, round-bottom flask reactor, followed by addition of 117.28 grams of 16.1% sodium pyrithione solution. The reaction mixture was stirred continuously, and the pH of the mixture monitored and recorded. The initial pH was 5, and it increased during the reaction to a final pH of 10.5 at room temperature. After approximately 4 hours of mixing, the contents of the flask was assayed for sodium pyrithione content by adding iron chloride and looking for the blue color of iron pyrithione. However, no blue color was found, indicating that the reaction was complete. A small amount (0.5% by weight) of stearic acid was added (to coat the particle) and mixed for 30 minutes.

The resulting copper pyrithione/cuprous oxide product was isolated by filtration. The resulting cake was then washed with water until the filtrate was free of ions as measured by conductivity. The cake was then dried in an vacuum oven at 30° C. overnight.

Microscopic examination indicated that many of the cuprous oxide particles were coated with adhering particles of copper pyrithione to form the desired composite particles plus sodium pyrithione.

Example 2

Preparation of a 1:10 Parts by Weight Copper Pyrithione: Cuprous Oxide Composite Particle Product Made Using Cuprous Oxide Plus Sodium Pyrithione This Example followed the same procedure as in Example 1, except 292.19 grams of a 70% aqueous fatty acid treated cuprous oxide slurry was charged into a 1000 ml 3-neck, round-bottom flask reactor. The cuprous oxide had been treated with 0.5 weight percent of stearic acid. No additional fatty acid was added later to coat the product.

The composite particle product was examined under a microscope consisted of needle-shaped copper pyrithione particles, cuprous oxide particles, and cuprous oxide particles coated with copper pyrithione.

Example 3

Preparation of a 1:5 Parts by Weight Copper Pyrithione: Cuprous Oxide Composite Particle Product Made Using Cuprous Oxide Plus Sodium Pyrithione 298.66 grams of a 70% aqueous fatty acid treated cuprous oxide slurry were charged into a 1000 ml 3-neck, round-bottom flask reactor. 234.61 grams of 16.1% crude sodium pyrithione solution were added, and the reaction mixture was continuously stirred as the pH of the mixture was monitored. After 4 hours of mixing the sodium pyrithione in the flask was assayed and found to be 0.0% indicating that the reaction was complete.

The resulting copper pyrithione/cuprous oxide composite product was isolated by filtration. The resulting cake was then washed with water until the filtrate was free of ions as measured by conductivity. The cake was then dried in an vacuum oven at 30° C. overnight.

The microscopic examination result weakens the application as originally stated.

Example 4

Preparation of a 1:20 Parts by Weight Copper Pyrithione: Cuprous Oxide Composite Particle Product Made Using Cuprous Oxide Plus Sodium Pyrithione 288.94 grams of a 70% aqueous fatty acid treated cuprous oxide slurry was charged into a 1000 ml 3-neck, round-bottom flask reactor, followed by addition of 58.55 grams of 16.1% sodium pyrithione solution. The reaction mixture was continuously stirred, the pH of the mixture was monitored, showing an initial pH of 5 and a final pH of 10.5. After 4 hours of mixing, no sodium pyrithione was found in the flask indicating that the reaction was complete.

The resulting copper pyrithione/cuprous oxide product was isolated by filtration. The resulting cake was then washed with water until the filtrate was free of ions as measured by conductivity. The cake was then dried in an vacuum oven at 30° C. overnight.

Example 5

Efficacy Testing of Composite Particle Product

The antifouling efficacy of the composition of Example 1 was evaluated by mixing 110 grams of it into 90 grams of a paint base. The commercial paint comprised:

TABLE 1

PAINT FORMULATION

| INGREDIENT | GRAMS | PERCENT |
|---|---|---|
| BENTONE SD-2 thickener | 1.7 | 0.85 |
| VAGH* resin | 4.99 | 2.50 |
| CUPRIC PYRITHIONE TO CUPROUS OXIDE IN A WEIGHT RATIO OF 1:10 | 110 | 55.00 |
| TRICRESYL PHOSPHATE | 4.3 | 2.15 |
| WOOD ROSIN | 10 | 5.00 |
| SILICA | 10.4 | 5.20 |
| SOLVENT MIXTURE** | 55.28 | 27.64 |
| DISPERBYK 163***dispersant | 3.33 | 1.67 |
| TOTAL | 200.00 | 100.00 |

*VAGH (polymer resin) = vinyl chloride-vinyl acetate-vinyl alcohol terpolymer, a product of Union Carbide Corporation.
**The solvent mixture used was a mixture of 40% by weight of xylene and 60% by weight of methyl-isobutyl ketone (MIBK)
***DISPERBYK 163 (dispersing agent) = a high molecular weight block copolymer, a product of BYK-Chemie.

This paint was painted onto fiberglass panels (8"×10") and (12"×6"), which were then submerged in seawater for eight months (and running) in Miami, Fla. The results to date show:

(1) the composite particle product's combination of cupric pyrithione and cuprous oxide is much more effective than either biocide alone and comparable in efficacy to a paint made using a simple mixture of these two biocides;

(2) relatively low level of cupric pyrithione (3%) and cuprous oxide (30%) containing paints in the composite particle perform better than the "cuprous oxide alone" controls;

(3) This composite particle product is effective in providing total antifouling performance against hard and soft fouling.

Figure 2:
FIG. 2 is a photomicrograph of composite particles of the present invention containing a core of cuprous oxide and a shell of copper pyrithione prepared by the method of the invention and viewed at 5,000× magnifications.

Pictures in the form of microphotographs of the cuprous oxide particles, and of the composite cuprous oxide/copper pyrithione particles, are provided in FIG. 1 and FIG. 2 respectively. FIG. 2 shows the attachment of small copper pyrithione particles to the surface of larger cuprous oxide particles.

The composite particle configuration is believed to provide complimentary biocidal efficacy for the following reason: CuPT is most effective against algae, while cuprous oxide provides complementary performance by strongly resisting barnacle formation but is relatively ineffective against algae. This combination product provided complete control of marine fouling after five months of exposure of the painted fiberglass panels to seawater. Other than tributyl tin, no other antifouling agent is known by the present inventors to provide this effectiveness against hard and soft fouling, and tin suffers from the diffusion layer 4b.

Proposed Examples

Proposed Example 6

Composite Particles Are Prepared Using Aluminum Oxide Plus Sodium Pyrithione

A beaker with a stirrer is charged with a slurry of 10.0 g (0.10 m) of aluminum oxide in 100 ml of distilled water. To this stirred slurry, at ambient temperature, is added dropwise over a period of one-half hour 11.8 g, 0.029-mole of a 40% solution of the sodium salt of 2-pyrithione. This mixture is stirred an additional 1 hr. at ambient temperature, the pH adjusted to 8.5 with dilute hydrochloric acid, and the slurry is filtered, washed with 3 times 50 ml of distilled water, or until essentially free of soluble pyrithione salt. It is then dried in a 40-50 C. oven overnight to yield 11.2 g powder. XRF analysis of the resulting composite composition indicates the presence of a pyrithione-containing coating on the water-insoluble core aluminum oxide substrate. The new composition also shows enhanced bioactivity toward algae, fungi, and bacteria, relative to the core material, when challenged in standard tests for such activity.

Proposed Examples 7-23

Composite Particles Are Prepared Using Various Metals, Metal Oxides or Metal Salts Plus Sodium Pyrithione Following the procedure of Example 6 above, the amount of the metal element or compound described in Table 2 is employed instead of the aluminum oxide used in Example 6. XRF analysis of the resulting composite composition powder (having a yield given in the last column of Table 2 for each example) indicates the presence of a pyrithione-containing coating on the water-insoluble core substrate. The new composition also shows enhanced bioactivity toward algae, fungi, and bacteria, relative to the core material, when challenged in standard tests for such activity.

TABLE 2

VARIOUS COMPOSITE PRODUCT COMBINATIONS

| | CORE COMPOUND COMPOSITION | (grams) | SHELL COMPOUND SODIUM PYRITHIONE REAGENT 40% aqueous (grams) | COMPOSITE PRODUCT YIELD DRY WEIGHT (grams) |
|---|---|---|---|---|
| 7 | Aluminum phosphate | 10 | 9.9 | 11.1 |
| 8 | Bismuth Oxide | 10 | 9.9 | 10.4 |
| 9 | Copper | 10 | 12.8 | 11.5 |
| 10 | Copper II Carbonate | 10 | 4.3 | 10.5 |
| 11 | Cuprous Oxide | 10 | 5.6 | 10.7 |
| 12 | Cupric Oxide | 10 | 10.1 | 11.2 |
| 13 | Copper I Selenide | 10 | 5.6 | 10.7 |
| 14 | Iron II Oxide | 10 | 11.2 | 11.8 |
| 15 | Iron III Oxide | 10 | 5.0 | 10.9 |
| 16 | Silver | 10 | 3.7 | 10.7 |
| 17 | Silver Oxide | 10 | 1.7 | 10.3 |
| 18 | Titanium Oxide | 10 | 20.2 | 12.1 |
| 19 | Zinc | 10 | 12.3 | 11.5 |
| 20 | Zinc Oxide | 10 | 9.9 | 11.2 |
| 21 | Zinc Selenide | 10 | 5.6 | 10.7 |
| 22 | Zirconium Oxide | 10 | 13.1 | 11.4 |

Proposed Example 24

Preparation of a Shampoo

An antidandruff shampoo is prepared using the composite biocide particles described in Example 20 having a core of zinc oxide and a shell of zinc pyrithione. The shampoo contains the following components:

| Component A: | |
|---|---|
| Magnesium aluminum silicate | 1.0% |
| Water | 41.0% |
| Hydroxypropyl methylcellulose | 0.8% |
| Component B: | |
| Zinc Pyrithione/zinc oxide composite particles, | 4.0% |
| Component C: | |
| Cocamide DEA | 1.0% |
| Component D: | |
| Triethanolamine lauryl sulfate, 40% | 40.0% |
| Triethanolamine, 99% | 3.2% |
| FD&C Blue No. 1 (0.2%) | 1.5% |
| FD&C Yellow No. 5 (0.1%) | 0.5% |
| Fragrance | q.s. |

The antidandruff shampoo composition was made as follows:

Component A was prepared by heating water to 70° C. and dissolving the other two components with stirring (about 1500 rpm). Component B was added, and stirring continued for 5 minutes. Stirring speed was reduce stirring to ~300 RPM. Component C was melted in a separate container, and added to the A/B mixture. The heat was removed and component D was added while the mixture cooled.

The present invention is intended to illustrate, but in no way limit the scope of the present invention. Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entirety.

What is claimed is:

1. A biocidal composition consisting of composite particles, each of said composite particles consisting of a shell, a core, and a fatty acid
    wherein said core is selected from surface oxidized copper powder, cuprous oxide, copper hydroxide, and combinations thereof, said shell consists of a copper pyrithione formed by reaction of pyrithione acid or a water-soluble salt of pyrithione with copper from said core, and said fatty acid is selected from the group consisting of stearic acid, oleic acid, glycerol, and combinations thereof,
    wherein said core has a water solubility of no greater than about 10 ppm,
    wherein said core is present in said composition in an amount of from about 99 to about 60% by weight of the composition, and
    wherein said copper pyrithione shell is present in an amount of from about 1 to about 40% by weight of the composition.

2. The composition of claim 1 wherein said copper pyrithione shell is from about 2 to about 20% by weight of the composition.

3. The composition of claim 2 wherein said copper pyrithione shell is from about 3 to about 14% by weight of the composition.

4. The composition of claim 1, wherein the copper pyrithione and the core are present within a weight range of ratios from 1:20 to 20:1 of copper pyrithione relative to the core.

5. The composition of claim 1 wherein the core is cuprous oxide and the shell is copper pyrithione.

6. The composition of claim 5 wherein the cuprous oxide to the copper pyrithione is in a weight ratio of from 5:1 to 15:1, and a coating diameter is about 1% of the particle.

7. The composition of claim 1 wherein said water-soluble salt of pyrithione is sodium pyrithione.

* * * * *